United States Patent [19]

Bates

[11] Patent Number: 4,772,268
[45] Date of Patent: Sep. 20, 1988

[54] TWO LUMEN HEMODIALYSIS CATHETER

[75] Inventor: Brian L. Bates, Bloomington, Ind.

[73] Assignee: Cook Incorporated, Bloomington, Ind.

[21] Appl. No.: 924,112

[22] Filed: Nov. 3, 1986

Related U.S. Application Data

[63] Continuation of Ser. No. 613,805, May 25, 1984, Pat. No. 4,643,711.

[51] Int. Cl.⁴ .............................................. A61M 5/32
[52] U.S. Cl. ...................................... 604/174; 604/43
[58] Field of Search .............................. 604/43–45, 604/272, 4–5, 174, 177, 27

[56] References Cited

U.S. PATENT DOCUMENTS

| | | | |
|---|---|---|---|
| D. 272,651 | 2/1984 | Mahurkar | 604/44 |
| 519,635 | 5/1894 | Kregel | 604/44 |
| 2,564,977 | 8/1951 | Hu | 604/44 |
| 4,134,402 | 1/1979 | Mahurkar | 604/272 |
| 4,203,436 | 5/1980 | Grimsrud | 604/44 |
| 4,352,354 | 10/1982 | Ujihara | 604/272 |
| 4,385,631 | 5/1983 | Uthmann | 604/43 |
| 4,451,252 | 5/1984 | Martin | 604/164 |
| 4,568,329 | 2/1986 | Mahurkar | 604/43 |
| 4,643,711 | 2/1987 | Bates | 604/4 |

FOREIGN PATENT DOCUMENTS 0195412 2/1908 Fed. Rep. of Germany ........ 604/43

Primary Examiner—C. Fred Rosenbaum
Assistant Examiner—Gene B. Kartchner
Attorney, Agent, or Firm—Woodard, Emhardt, Naughton, Moriarty & McNett

[57] ABSTRACT

A dual lumen hemodialysis catheter. The catheter includes a tube having a circular external cross section which is rotatably received within a fitting. The fitting may be attached to the patient by sutures or the like and rotatably mounts the tube of the catheter. Stop means are provided on opposite sides of the fitting preventing the tube of the catheter from moving longitudinally relative to the fitting. The catheter may be rotated relative to the fitting in order to readjust the rotational position of the tube inside the patient's blood vessel without longitudinal movement of the tube. The catheter is cut off at its distal end perpendicularly to the length of the tube in order to define the mouth of one lumen. The tube is tapered from the cut off distal end to a point proximal of the distal end, said point being approximately 3 cm from the distal end. The taper of the tube defines at least a portion of the mouth of the second lumen.

10 Claims, 1 Drawing Sheet

U.S. Patent  Sep. 20, 1988  4,772,268
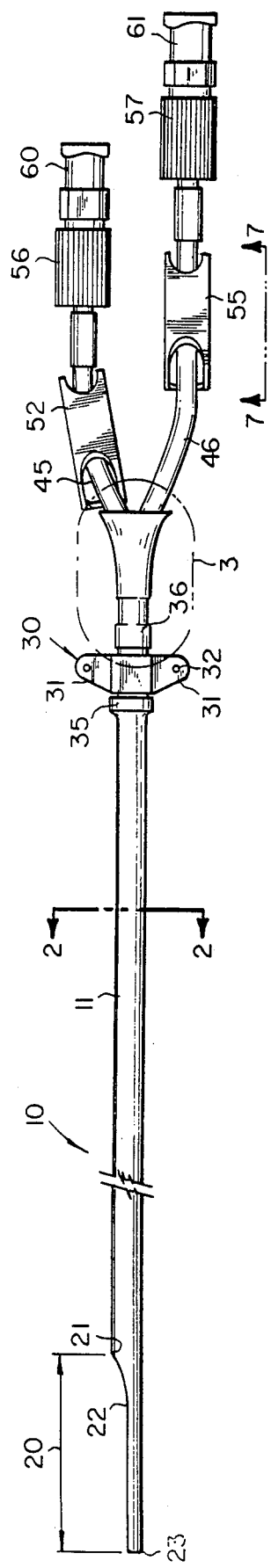
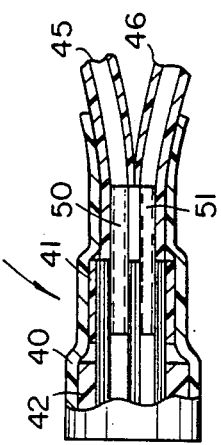
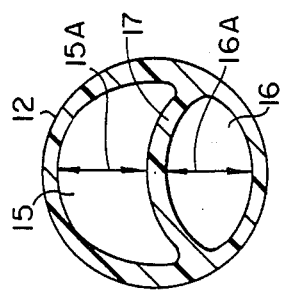
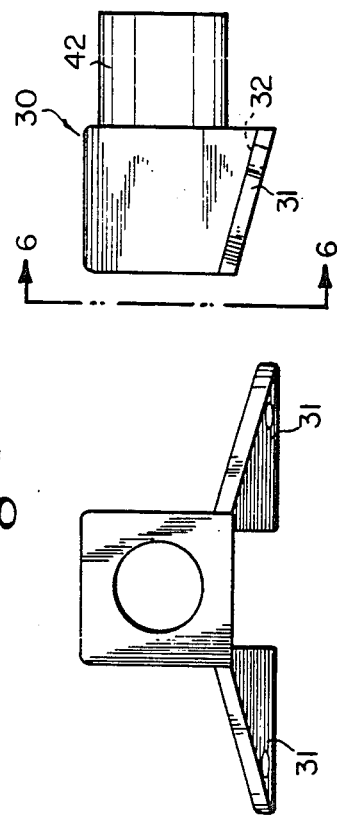

TWO LUMEN HEMODIALYSIS CATHETER

REFERENCE TO RELATED APPLICATIONS

This application is a continuation of U.S. patent application Ser. No. 613,805, filed on May 25, 1984 by and issued on Feb. 17, 1987 as U.S. Pat. No. 4,643,711 to the same inventive entity, and entitled TWO LUMEN HEMODIALYSIS CATHETER.

BACKGROUND OF THE INVENTION

The present invention is related generally to intravenous catheters and more particularly to a catheter particularly adapted for hemodialysis.

DESCRIPTION OF THE PRIOR ART

There is available a number of catheter designs for use in the simultaneous introduction of fluid into the body and withdrawal of fluid from the body. Such catheters are particularly useful in hemodialysis. Two such designs are illustrated in the U.S. patent to Jacobsen et al. U.S. Pat. No. 4,180,068 and the U.S. patent to Mahurkar, U.S. Pat. No. 4,134,402. The devices of each of these patents are designed in such a manner as to promote insertion of the device into the vessel. Thus, the Mahurkar device includes a beveled edge which slopes away from the needle to facilitate insertion of the needle. Also, the Jacobsen device has a built in trocar for piercing in order to insert the catheter. Such features do not necessarily aid in proper operation of the catheter when inserted and in place and in some instances may interfere with such proper operation. It is desirable that the catheter be designed in such a fashion as to reduce to as low an amount as possible the mixing of the dialyzed and the undialyzed blood. It is also desirable that the catheter be designed so as to promote and permit free flow of blood into and out of the catheter.

SUMMARY OF THE INVENTION

One embodiment of the present invention might involve a catheter including a tube having a circular external cross section. A fitting is rotatably mounted on the tube so as to surround the circular cross section. The tube is rotatable about its axis relative to the fitting. The fitting has a projection which is adapted to be attached to the skin of the patient whose blood vessel is percutaneously catherized by the catheter. There is also provided stop means fixed to the tube on opposite sides of the fitting and preventing the tube from moving longitudinally relative to the fitting. The above described structure makes possible the catheter being rotated relative to the fitting in order to readjust the rotational position of the tube inside the blood vessel without longitudinal movement of the tube and without separating the attachment of the projection to the skin.

Still another embodiment of the invention may additionally include a pair of side by side lumens in the tube with one of the lumens extending all the way to the distal end of the catheter. The catheter is cut off at the distal end perpendicularly to the length of the tube in order to define the mouth of one lumen. The tube is tapered from the cut off distal end to a point proximal of the distal end, said point being approximately 3 cm from the distal end. The taper of the tube defines at least a portion of the mouth of the second lumen.

BRIEF DESCRIPTION OF THE DRAWINGS

FIG. 1 is a side elevation of a two lumen hemodialysis catheter embodying the present invention.

FIG. 2 is a enlarged section taken along the lines 2—2 of FIG. 1 in the direction of the arrows.

FIG. 3 is an enlarged side elevation of the portion of the structure marked 3 in FIG. 1 with areas broken away to show the internal construction by a sectional view taken axially of the catheter.

FIG. 4 is a top plan view of the distal end of the catheter with the view being taken at 90° to the view of FIG. 1.

FIG. 5 is an enlarged side elevation of a portion of the structure illustrated in FIG. 1.

FIG. 6 is a view taken along the line 6—6 of FIG. 5 in the direction of the arrows.

FIG. 7 is a view taken along the line 7—7 of FIG. 1 in the direction of the arrows and showing a plastic clamp forming a part of the structure.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring more particularly to the drawing, there is illustrated a two lumen hemodialysis catheter 10 which includes a tube 11 having an external circular cross section 12 as shown, for example, in FIG. 2. Even though the external configuration of the tube is cylindrical, the tube has a pair of lumens 15 and 16. The lumen 15 is separated from the lumen 16 by a wall 17. The lumen 16 has a generally elliptical cross section, whereas the lumen 15 is generally of less-than-half-moon shape and generally curves around the lumen 16 and has a somewhat larger cross sectional area than the lumen 16. In one specific embodiment of the invention, the dimension 16A of the lumen 16 is 0.055 inches and the dimension 15A of the lumen 15 is 0.068 inches. Such two lumen tubing is available commercially and may be purchased, for example, from Sabin Corporation of 617 South Curry Pike, P. O. Box 788, Bloomington, Ind. 47401 under the model designation PUTL-12.

In order to manufacture the distal tip of the catheter of the present invention, the large lumen 15 is basically cut off for a 3 cm distance. Thus the distance 20 is 3 cm. This cutting off procedure produces a taper from the point 21 to the point 22 which point is approximately 2 cm from the distal tip 23 of the catheter. The catheter is cut off at the distal end 23 perpendicularly to define the mouth of the lumen 16.

The catheter of the present invention is placed into the blood vessel by the use of the Desilet-Hoffman procedure. The catheter of the present invention and specifically the tube 11 is made out of a relatively flexible plastic material so that it does not have sufficient stiffness and rigidity nor sharpness on its own to be inserted into the blood vessel. The procedure for inserting the catheter into the blood vessel involves the use of a needle and a wire guide. After the needle has been inserted into the blood vessel, the wire guide is placed through the needle into the blood vessel. Next the needle is removed from the wire guide and a dilator with an overlying sheath is slid over the wire guide into the blood vessel. The sheath may be one such as the sheath disclosed in the Osborne patent, U.S. Pat. No. 4,306,562 and reissue application Ser. No. 443,321 now U.S. Pat. No. RE31855. The above description of the Desilet-Hoffman procedure is illustrated in FIGS. 3-10 of U.S. Pat. No. 4,306,562 and reissue application Ser. No. 443,321 now U.S. Pat. No. RE31855. The wire guide and dilators are removed from the sheath and the catheter of the present invention is inserted into the sheath into the blood vessel. Lastly the sheath is removed from the catheter by tearing it longitudinally as described in U.S. Pat. No. 4,306,562 and reissue application Ser. No. 443,321.

The catheter 10 further includes a fitting 30. The fitting 30 is shown in detail in FIGS. 5 and 6 as having a pair of projections 31. When the present catheter is in use, the projections 31 are sutured to the skin of the patient by use of the apertures 32. Stop means 35 and 36 are provided on opposite sides of the fitting 30 so as to prevent the tube from moving longitudinally relative to the fitting. The stop means 36 consists of a tubular length of shrink tube 40 as well as an additional shorter length of shrink tube 41. The shrink tube 41 is mounted upon the tube 11. The shrink tube 40 is mounted upon the tube 41 and surrounds the portion 42 of the fitting as well as tubes 45 and 46 which are connected to the lumens 15 and 16 by metal tubes 50 and 51. The tubes 50 and 51 are telescoped within the lumens 15 and 16 and the tubes 45 and 46, respectively. All of the structure, except for the portion of the shrink tube 40 that surrounds the collar 42 of the fitting 30, is suitably attached together by superglue and urethane bond. The portion of the shrink tube 40 that surrounds the collar 42' of the fitting 30 allows rotation of the tube 11 within the fitting 30 but does provide some resistance to such rotation by the engagement of the shrink tube 40 with the collar 42.

There is also provided suitable clamps 52 and 55 for closing off the flow of fluid through the tubes 45 and 46, respectively. These clamps are identical and are formed of flexible plastic material. Representative clamp 55 is shown in front elevation in FIG. 7. Mounted on the ends of tubes 45 and 46 are female Luer lock adapters 60 and 61 threadedly mounted thereon for coupling the tubes 45 and 46 to a dialysis machine. The Luer lock adapters permit Luer lock attachment. Such adapters 60 and 61 are commercially available from Cook Incorporated, 925 South Curry Pike, Bloomington, Ind. 47402. Alternatively, other coupling means may be used.

It will be evident from the above description that this invention provides an improved catheter for use in hemodialysis. The catheter permits easy adjustment by the user because all that is required to change the orientation of the catheter in the blood vessel is rotation of the catheter relative to the fitting 30 causing the distal end of the catheter to be reoriented relative to the blood vessel. It will also be evident from the above description that the catheter of this invention has a different construction of its distal tip. This different construction has been found to produce a very substantially improved operation of the catheter when used for hemodialysis.

In hemodialysis the lumen 16, i.e., the distal port is used to inject the dialyzed blood. The lumen 15, i.e., the proximal port is used to withdraw the undialyzed blood.

In conventional catheters used for hemodialysis, there is a considerably amount of mixing between the dialyzed blood and the undialyzed blood. Thus, users report that in conventional hemodialysis catheters about 20 to 25% of the blood withdrawn is dialyzed blood. With the use of the present design, evaluators have reported 3.1% of the blood withdrawn is dialyzed blood.

It should also be mentioned that the cutting off procedure mentioned above of the large lumen 15 increases the flexibility of the tip of the catheter. Although there is no present direct scientific evidence to support the following, it is believed that increased flexibility reduces the possibility of the tip eroding through tissue. It should also be noted that the present design has no side ports and instead has two straight through lumens which open at their distal ends either directly axially or at least partially in an axial direction, that is, longitudinally of the catheter. It is believed that such straight through lumens with no side ports reduces turbulence and results in lower recirculation percentage although there is presently no direct scientific evidence to support such conclusion.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed:

1. A catheter comprising a tube having a circular external cross section, a fitting rotatably mounted on said tube so as to surround said cross section, said tube being fully 360° rotational about its axis relative to said fitting, said fitting having a projection adapted to be attached to the skin of a patient whose blood vessel is percutaneously catheterized by said catheter, and stop means fixed to said tube on opposite sides of said fitting and preventing said tube from moving longitudinally relative to said fitting while said tube is fully 360° rotational relative to said fitting, whereby said catheter can be rotated relative to said fitting in order to readjust the rotational position of said tube inside the blood vessel without longitudinal movement of the tube and without separating the attachment of the projection to the skin.

2. The catheter of claim 1 which is a two lumen hemodialysis catheter.

3. The catheter of claim 2 wherein said lumens are side-by-side, said catheter having a distal end, one of the lumens extending all the way to the distal end of said catheter, said catheter being cut off at said distal end perpendicularly to the length of said tube to define the mouth of said one lumen, said tube being tapered from said cut off distal end to a point proximal of said distal end, said taper of said tube defining at least a portion of the mouth of said second lumen.

4. The catheter of claim 3 wherein the cross sectional area of the one lumen is greater than the cross sectional area of the other lumen.

5. The catheter of claim 3 wherein the cross sectional area of said one lumen is elliptical and the cross sectional area of said other lumen is generally of less-than-half-moon shape and generally curves around the one lumen.

6. The catheter of claim 3 wherein said lumens are separated from one another by a wall, said one lumen having a cross sectional area which is elliptical, said other lumen being of generally less-than-half-moon shape and generally curving around the one lumen, the central dimension across said one lumen taken perpendicular to said wall being 0.055 inches, the central dimension across said other lumen taken perpendicularly to said wall being 0.068 inches.

7. The catheter of claim 3 in which the lumens open at the distal end at least partially in the direction of the length of the tube.

8. The catheter of claim 6 wherein the cross sectional area of the one lumen is greater than the cross sectional area of the other lumen.

9. The catheter of claim 7 in which the side walls of the tube are continuous and the only openings therein between said fitting and said distal end are said mouths.

10. The catheter of claim 7 having a solid wall construction all the way to both lumen mouths.

* * * * *